(12) United States Patent
Mahabadi et al.

(10) Patent No.: US 9,007,075 B2
(45) Date of Patent: *Apr. 14, 2015

(54) CONTACTLESS CONDUCTIVITY DETECTOR

(75) Inventors: Kambiz Ansari Mahabadi, Singapore (SG); Isabel Rodriguez Fernandez, Singapore (SG); Chee Yen Lim, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 696 days.

This patent is subject to a terminal disclaimer.

(21) Appl. No.: 13/057,922

(22) PCT Filed: Aug. 7, 2009

(86) PCT No.: PCT/SG2009/000277
§ 371 (c)(1),
(2), (4) Date: Feb. 7, 2011

(87) PCT Pub. No.: WO2010/016807
PCT Pub. Date: Feb. 11, 2010

(65) Prior Publication Data
US 2011/0140721 A1 Jun. 16, 2011

Related U.S. Application Data

(60) Provisional application No. 61/087,000, filed on Aug. 7, 2008.

(51) Int. Cl.
G01R 27/26 (2006.01)
G01N 27/447 (2006.01)

(52) U.S. Cl.
CPC .................... *G01N 27/4473* (2013.01)

(58) Field of Classification Search
CPC .......... G01N 27/44791; G01N 27/453; G01N 27/44769
USPC ........................................................ 324/688
See application file for complete search history.

(56) References Cited

U.S. PATENT DOCUMENTS 3,862,571 A * 1/1975 Vogel ........................ 73/304 C
3,901,079 A * 8/1975 Vogel ........................ 73/304 C
(Continued)

FOREIGN PATENT DOCUMENTS

| JP | 2009-244182 | * 10/2009 | ............. G01N 27/62 |
| WO | WO00/16907 A1 | 3/2000 | |
| WO | WO00/17630 A1 | 3/2000 | |
| WO | WO00/75650 A1 | 12/2000 | |
| WO | WO2005/033685 A2 | 4/2005 | |

OTHER PUBLICATIONS

Kawaura, JP2009-244182, Machine Translation from JPO, p. 1-12, attached to abovementioned JPO patent.*
(Continued)

*Primary Examiner* — Thomas F Valone
(74) *Attorney, Agent, or Firm* — Faegre Baker Daniels LLP

(57) ABSTRACT

The contactless conductivity detector in one embodiment includes a microfluidic chip having a channel (102) thereon and four detection electrodes: first and second emitting electrodes (100a, 101a), and first and second receiving electrodes (100b, 101b). The channel (102) is defined by channel walls. The first emitting electrode (100a) and the first receiving electrode (100b) are adjacent a first channel wall, and the second emitting electrode (101a) and the second receiving electrode (101b) are adjacent a second channel wall, the second channel wall being opposite the first channel wall.

16 Claims, 11 Drawing Sheets

(56) References Cited

U.S. PATENT DOCUMENTS

| | | | |
|---|---|---|---|
| 5,049,878 A * | 9/1991 | Stern | 340/870.4 |
| 5,138,880 A * | 8/1992 | Lee et al. | 73/304 C |
| 5,455,418 A | 10/1995 | Hogan | |
| 6,748,804 B1 | 6/2004 | Lisec et al. | |
| 6,823,731 B1 * | 11/2004 | Lin | 73/304 C |
| 2002/0031838 A1 * | 3/2002 | Meinhart et al. | 436/514 |
| 2005/0109621 A1 | 5/2005 | Hauser et al. | |
| 2009/0242754 A1 * | 10/2009 | Kawaura | 250/288 |
| 2012/0160691 A1 * | 6/2012 | Mahabadi et al. | 204/603 |
| 2013/0172667 A1 * | 7/2013 | Craig | 600/35 |

OTHER PUBLICATIONS

Toth, A planar capacitive precision gauge for liquid-level and leakage detection, IEEE Trans. on Inst. and Meas., V. 46, No. 2, 1997, p. 644.*

International Search Report for International Application No. PCT/SG2009/000277, issued by the Australian Patent Office on Oct. 27, 2009.

International Preliminary Report on Patentability for International Application No. PCT/SG2009/000277, issued by the Australian Patent Office on May 28, 2010.

* cited by examiner

CONTACTLESS CONDUCTIVITY DETECTOR

CROSS-REFERENCE TO RELATED APPLICATIONS

This application is a U.S. National Phase Application of PCT International Application No. PCT/SG2009/000277, filed on Aug. 7, 2009, which claims the benefit of U.S. Application Ser. No. 61/087,000, filed on Aug. 7, 2008, both of which are expressly incorporated by reference herein.

FIELD OF THE INVENTION

The present invention relates to a contactless conductivity detector, and more particularly, but not exclusively, to a device for analysing and detecting analytes or ionic compounds using capacitively-coupled contactless conductivity detection (C4D).

BACKGROUND OF THE INVENTION

Lab-on-a-chip (LOC) based device requirements for analyte detection are sensitivity, universality and portability. To this date, these conditions have not been fully met and detection remains the main challenge in the development of LOC technology. Optical detectors, including fluorescence detection, have demonstrated the highest sensitivity. However, optical detectors are not universal and not easily made portable due to the size of the light sources. The use of electrochemical methods is well-suited for integration into portable systems, but they are less sensitive and prone to interferences. From the group of electrochemical sensors, C4D detectors are the most appealing as they fulfill the requirements of portability, universality for charged analytes and acceptable sensitivity.

The principle of C4D in combination with electrophoresis will now be described with reference to FIG. 1. FIG. 1 shows an arrangement of two external metal electrodes 100a, 100b in close proximity to an electrophoretic separation channel 102 in a microfluidic chip 104. The microfluidic chip 104 comprises two polymer sheets, namely top sheet 104a and bottom sheet 104b. The top sheet 104a provides access to reservoirs as will be described below, and the bottom sheet 104b provides the separation channel 102 that has been hot embossed into the bottom sheet 104b. In use, a run buffer reservoir 107, a first sample reservoir 109 and an outlet reservoir 111 of the microfluidic chip 104 are filled with electrophoretic run buffer solution, and a second sample reservoir 113 is filled with target analytes, typically ionic species dissolved in the run buffer solution. A separation voltage is then applied between the second sample reservoir 113 and the first sample reservoir 109. This drives 'plugs' of ions 114 into the separation channel 102. Subsequently, the separation voltage is applied between the run buffer reservoir 107 and the outlet reservoir 111 with all other reservoirs floating. This causes the plugs of ions 114 to be driven towards the electrodes 100a, 100b for detection.

The two external metal electrodes 100a, 100b and the electrophoretic separation channel 102 together form the C4D cell or detection cell. When the upstream/emitting electrode 100a emits an AC signal through the channel 102, it is capacitively captured by the downstream/receiving electrode 100b. The electrodes 100a, 100b are in the same plane and are attached to a top plate that seals the channel 102 and are typically placed in an anti-parallel configuration with respect to the length of the channel 102. The applied AC signal (typically 50-600 kHz) from the emitting electrode 100a capacitively couples through the channel 102 to the receiving electrode 100b, resulting in a small current that is amplified by an amplifier 106, rectified and offset-corrected using a rectifier 108, filtered and that undergoes data acquisition using a data acquisition tool (DAQ) 110 and finally recorded in a computing device 112 or other storage device as a DAQ graph.

The C4D cell can be considered as a combination capacitor-resistor-capacitor (CRC) electrical circuit, where the electrodes 100a, 100b and the channel's electric double layer form the capacitors, and the section of the channel 102 between the electrodes 100a, 100b forms the resistor. When a plug of ions 114 is driven through the section of the channel between the electrodes, the measured impedance of the system changes instantaneously because of change in the resistance due to the different conductivity of ionic species passing through the electrodes with the background electrolyte. In practical terms, this leads to a sudden change in the zero leveled output voltage or a peak in the DAQ graph. By electrophoresis, separated plugs of ions can be driven through the C4D cell at different times and the corresponding signal recorded, thus obtaining separated peaks according to the times at which the ions cross the C4D cell. Each peak is related by time to a specific ion, and the area under the peaks is related to the concentration of the specific ion. C4D in combination with electrophoresis therefore provides qualitative and quantitative analysis.

The C4D cells reported to date use two electrodes placed externally over the separation channel. An example is illustrated in FIGS. 2(a) and (b), which respectively show a perspective view and plan view of a conventional detection cell. As noted earlier, electrodes 100a, 100b in conventional detectors are fixed to a top plate 200 that seals the separation channel 102 and are typically placed in an anti-parallel configuration with respect to the channel 102. In this configuration, the capacitance coupling to the solution in the channel 102 is inefficient and requires a high frequency and high voltage to couple the signal to detect low concentration samples. High frequencies, however, result in stray capacitance having a more significant effect. Changes in the conductivity of the solution will then only result in a small change over the background signal.

To reduce or eliminate the stray capacitance, different strategies have been employed such as placing a ground plane 202 between the electrodes 100a, 100b to shield their direct crosstalk (as shown in FIGS. 2(a) and (b)). However, while these strategies decrease the stray capacitance somewhat, the resulting detection sensitivity remains limited.

One alternative option to improve capacitance is to increase the magnitude of the AC voltage. However, high voltage levels are difficult to produce and are not safe to handle in portable systems. Another option to have increased capacitance is to use relatively large electrodes or detection lengths, but these approaches severely decrease resolution.

Without compromising resolution, one effective way to increase sensitivity in capacitive coupling detection is to reduce the distance between the electrodes and the detection area or the section of the channel between the electrodes (also known as the 'detection cell volume'). Known arrangements have achieved this by either: (i) scribing off some portion from the chip surface so that electrodes can be disposed nearer to the channel, or (ii) incorporating electrodes within the chip (integrated chip) during the microfabrication so that they are close enough to the channel. These approaches are either inaccurate (for option (i) above) or require complex fabrication processes (for option (ii) above).

SUMMARY OF THE INVENTION

The present invention is defined in the independent claims. Some optional features of the present invention are defined in the dependent claims.

In general terms, the present invention relates to the use of emitting electrodes positioned or positionable adjacent to and on opposite sides of a microfluidic channel, and receiving electrodes adjacent to and positioned or positionable on opposite sides of a microfluidic channel.

In one specific expression, the present invention relates to a contactless conductivity detection cell comprising: a microfluidic chip having a channel defined by channel walls, first and second emitting electrodes, and first and second receiving electrodes, wherein the first emitting electrode and the first receiving electrode are adjacent a first channel wall, and the second emitting electrode and the second receiving electrode are adjacent a second channel wall, the second channel wall being opposite the first channel wall.

Preferably the emitting electrodes and receiving electrodes are substantially planar and substantially parallel to each other.

Preferably the emitting electrodes are placed one on top and one at the bottom of the chip passing over the channel, and are configured to act as electrostatic image of each other to concentrate and focus signals from each other into a detection cell volume of the detection cell. Similarly, the receiving electrodes are preferably placed one on top and one at the bottom of the chip covering channel, and are configured to act as electrostatic images of each other to extract coupled signal from a detection cell volume of the detection cell.

Preferably the electrodes are each positioned at a distance of between 75 µm and 1000 µm from the channel and preferably the microfluidic chip has a thickness in the range of 30 µm to 1 mm.

Preferably the detection cell further comprises a first ground plane between the emitting electrodes and the receiving electrodes, and a grounded metal housing containing the emitting electrodes, the receiving electrodes and the first ground plane.

Preferably the detection cell further comprises a second ground plane configured to shield the emitting electrodes and the receiving electrodes from interferences from electronic components housed in the grounded metal housing while keeping a very close distance between the receiving electrodes and the receiving amplifier encased in a second shielded housing.

Preferably at least part of the channel between the emitting electrodes and the receiving electrodes has a restricted sub-micron-sized or nano-sized width/cross-section.

In one form, the first emitting electrode and the first receiving electrode are preferably arranged on or in a top plate of the microfluidic chip, and wherein the second emitting electrode and the second receiving electrode are adjacent a base of the channel. In another form, the first emitting electrode and the first receiving electrode are preferably arranged adjacent one side of the channel, and wherein the second emitting electrode and the second receiving electrode are arranged adjacent an opposite side of the channel.

Preferably the detection cell further comprises multiple parallel channels, each channel having a pair of emitting electrodes and a pair of receiving electrodes, wherein all of the emitting electrode pairs are connected to a single input.

In another specific expression, the present invention relates to a portable electrophoretic micro fluidic system and a contactless conductivity detection system comprising: a platform having an opening configured to receive a microfluidic chip having a channel defined by channel walls, a cover configured to close at least part of the opening, first and second emitting electrodes, and first and second receiving electrodes, wherein the first emitting electrode and the first receiving electrode are configured to be positioned adjacent a first channel wall, and the second emitting electrode and the second receiving electrode are configured to be positioned adjacent a second channel wall, the second channel wall being opposite the first channel wall.

Preferably the cover is configured to secure at least part of a microfluidic chip between the cover and the base of the opening.

Preferably the second emitting electrode and the second receiving electrode are positioned on or adjacent the base of the opening.

Preferably the first emitting electrode and the first receiving electrode are positioned on or adjacent an internal surface of the cover. Preferably the cover includes a holder on the internal surface, and wherein the first emitting electrode and the first receiving electrode are positioned on the holder.

Preferably the holder is resiliently coupled to the cover and is configured to press the first emitting electrode and the first receiving electrode against a microfluidic chip.

Preferably the detection system further comprises one or more slots to allow a microfluidic chip to be inserted into the opening.

Preferably the cover is selected from a group consisting of: a pivotable cover and a detachable cover.

Preferably the emitting electrodes and/or the receiving electrodes are movable along the channel.

Preferably the opening is configured to allow a microfluidic chip to be movable within the opening.

Preferably the detection system further comprises a current-to-voltage converter adjacent and connected to the receiving electrodes, and a rectifier, low-pass filter, and offset circuit connected to the current-to-voltage converter. Preferably the detection system further comprises an alternating current function generator adjacent and connected to the emitting electrodes, and a miniaturized high voltage power supply. Preferably the detection system further comprises detection electronics arranged on a circuit that comprises a top layer and a bottom layer, the top layer being isolated from the bottom layer.

In yet another specific expression, the present invention relates to a capacitive coupled contactless conductivity detection cell comprising: a microfluidic chip having a channel, and detection electrodes placed in a top-bottom geometry and in close proximity to the channel.

In still another specific embodiment, the present invention relates to a capacitive coupled contactless conductivity detection cell comprising: detection electrodes placed in a top-bottom geometry in a housing, a detection area located within the housing, a Faraday shield, and a grounded metal housing, wherein the electrodes are shielded from direct cross talk or external noise by the Faraday shield and the grounded metal housing.

Preferably the detection electrodes comprise two emitting electrodes and two receiving electrodes.

Preferably the emitting electrodes are placed one on top and one at the bottom of the channel, and are configured to act as electrostatic images of each other to concentrate and focus the signals from each other into a detection cell volume of the detection cell.

Preferably the receiving electrodes are placed one on top and one at the bottom of the channel, and are configured to act as electrostatic images of each other to extract coupled signals from a detection cell volume of the detection cell.

Preferably the detection electrodes comprise two emitting electrodes and two receiving electrodes separated by the Faraday shield and located in the grounded metal housing.

Preferably the housing holds a microfluidic chip inserted into a holder within the emitting and receiving electrodes.

Preferably the emitting and receiving electrodes are placed close to the separation channel, and are movable by a cover to adjust a detection cell volume of the detection cell.

Preferably the detection area is adjustable by moving the microfluidic chip within the emitting and receiving electrodes.

As will be appreciated from the above summary, specific aspects of the present invention provide a C4D cell with improved sensitivity and detection limit compared to detection cells of the state of the art. A benefit of improving sensitivity is that the present invention can be implemented using lower power inputs than previously employed. The gap distance between the detection electrodes is made adjustable in accordance with certain embodiments of the invention, hence the detection cell length and thus the limit of detection (LOD, which determines sensitivity) and/or peak separation (which determines resolution) can be fine-tuned depending on demands of the specific application Where a shielded housing is provided containing all the necessary electronics and the C4D cell, an enhanced signal-to-noise ratio (S/N) is able to be obtained, which results in a highly sensitive electrophoretic device. Embodiments of the present invention also provide a C4D detection device that has low power requirements. These and other related advantages will be readily apparent to skilled persons from the description below.

BRIEF DESCRIPTION OF THE FIGURES

Non-limiting embodiments of the present invention will now be described by way of example with reference to the accompanying figures in which.

DETAILED DESCRIPTION OF THE PREFERRED EMBODIMENTS

Figure 1:
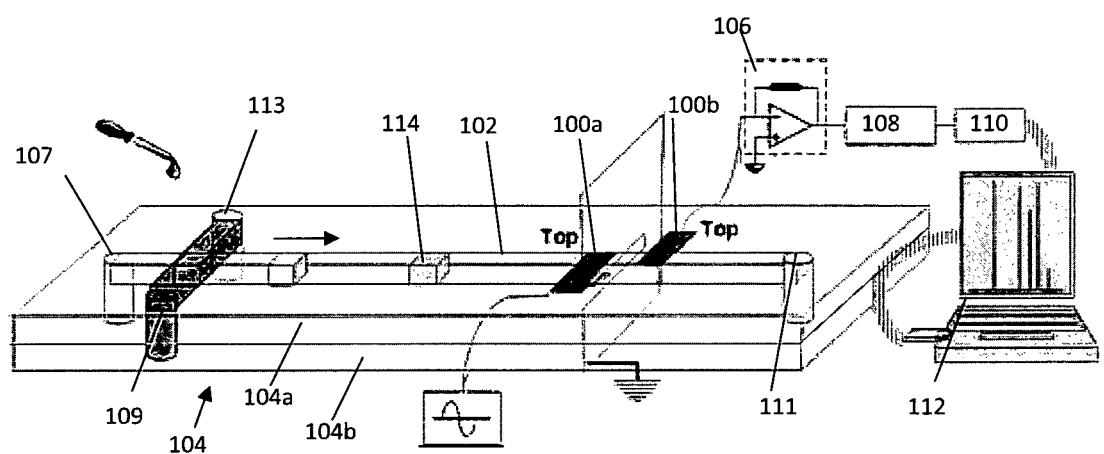
FIG. 1 is a schematic diagram of a conventional LOC-C4D analytical system comprising an electrophoretic separation microchip and C4D detection electrodes.
Figure 2:
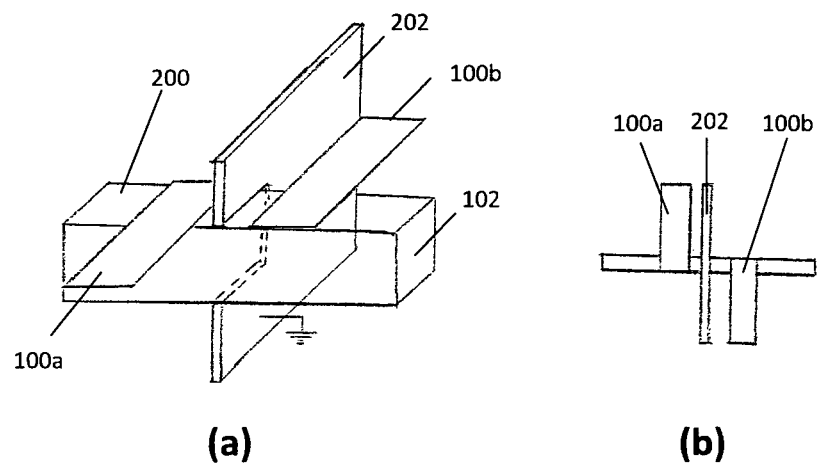
FIGS. 2(a) and 2(b) are diagrams of a conventional C4D detection cell electrode arrangement.
Figure 3:
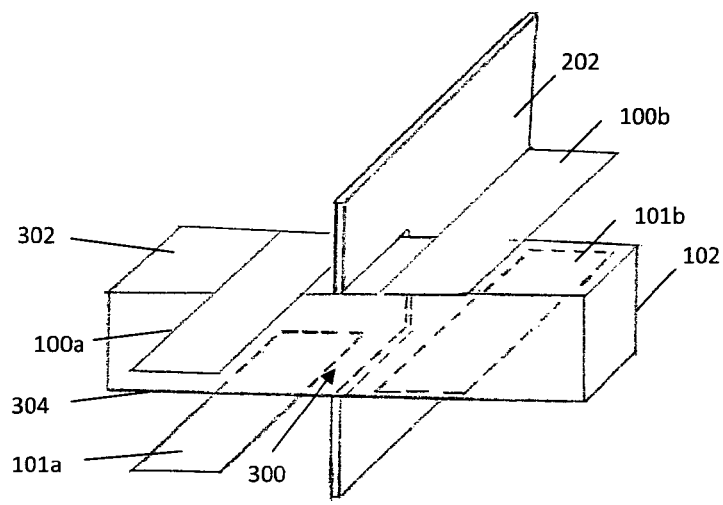
FIG. 3 is a diagram of the C4D detection cell electrode arrangement of the present invention.

Referring to FIG. 3, the present invention in one preferred embodiment comprises a capacitively-coupled contactless conductivity detector comprising a microfluidic electrophoretic chip (not shown) having a separation channel 102 thereon, first and second emitting electrodes 100a, 101a, and first and second receiving electrodes 100b, 101b on the chip and adjacent the separation channel 102. Between the emitting electrodes 100a, 101a and the receiving electrodes 100b, 101b is a detection area generally indicated with arrow 300. As will be described in detail below, the first and second emitting electrodes 100a, 101a are configured to concentrate signals emitted from one another to the detection area 300, and the first and second receiving electrodes 100b, 101b are configured to extract signals from the detection area 300.

It can be seen from FIG. 3 that the separation channel 102 is defined by channel walls, with the first emitting electrode 100a and the first receiving electrode 100b being located adjacent a first channel wall 302. The first channel wall 302 forms part of the top plate of the microfluidic chip. The second emitting electrode 101a and the second receiving electrode 101b are located adjacent a second channel wall 304, which is opposite the first channel wall 302. This allows for maximum concentration and extraction of signals within the detection area 300. The receiving electrodes 100b, 101b are displaced along the length of the channel 102 from the emitting electrodes 100a, 101a, with the area in the channel 102 between the emitting and receiving electrodes defining the detection area 300. The second channel wall 304 forms part of the base of the channel 102 in the preferred embodiment. For ease of reference, this arrangement or geometry of electrodes will herein be referred to as a top-bottom geometry. Accordingly, the first emitting electrode 100a is a top emitting electrode, the second emitting electrode 101a is a bottom emitting electrode, the first receiving electrode 100b is a top receiving electrode and the second receiving electrode 101b is the bottom receiving electrode. Also for ease of reference, the emitting and receiving electrodes will collectively be referred to as detection electrodes.

All of the detection electrodes 100a, 100b, 101a, 101b are substantially planar, parallel to each other, and are arranged in close proximity to the detection area 300 to enhance the coupling of the excitation signals into the channel 102 and to prevent loss of signals to be extracted. The distance between the detection electrodes and the channel is preferably between 75 μm-150 μm. This is, however, a non-limiting range as the distance may be set anywhere from 1 μm-1000 μm depending on a variety of factors (e.g. chip thickness, method of electrode placement, application desired etc). To avoid direct coupling or crosstalk between the emitting and receiving electrodes, a ground plane 202 is provided.

The separation channel 102 of the preferred embodiment is fabricated in a thin plastic (e.g. 30 μm-1 mm, a non-limiting example being a 125 μm polymeric) or glass film with the detection electrodes being disposed (e.g. by sputtering) on hot embossed sealed channels on the film that are arranged to allow positioning of the detection electrodes near the detection cell volume. The use of thin microfluidic chips allows the placing of the detection electrodes in close proximity to the channel so as to achieve a large capacitance, and thus, a larger signal output. It is, however, not essential that the detection electrodes be printed on the microfluidic chip itself. An alternative placement of the detection electrodes will be described in further detail with reference to the portable detector embodiment in FIG. 13.

Figure 4:
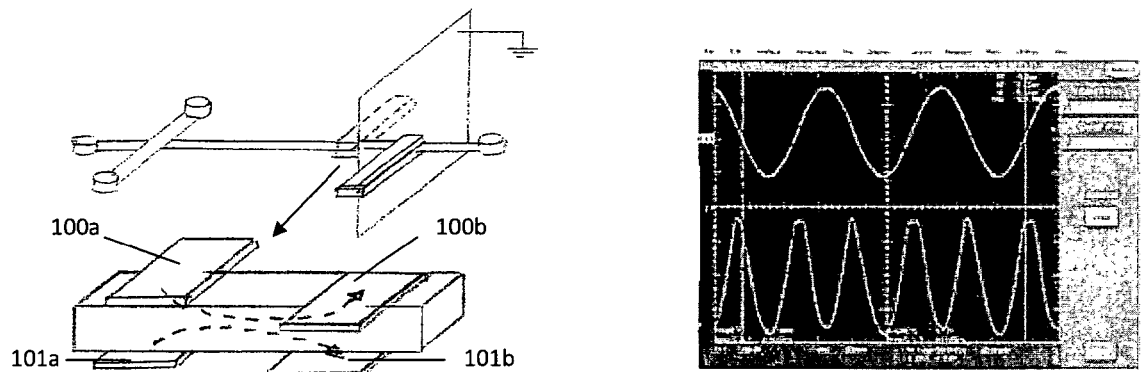
FIG. 4 is a diagram of the electrode arrangement of the present invention and the output signals from the electrode arrangement of the present invention.
Figure 5:
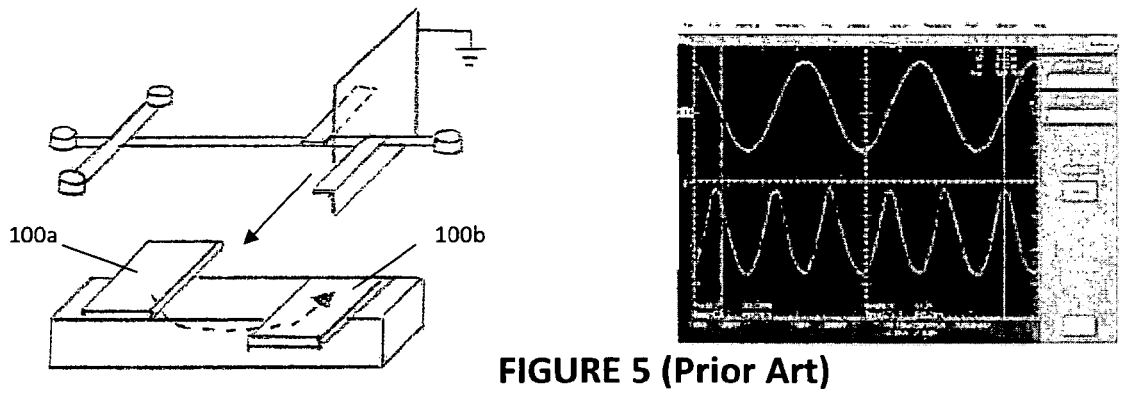
FIG. 5 is a diagram of a conventional electrode arrangement and the output signals from the conventional electrode arrangement.

As will be appreciated from FIGS. 4 and 5, the electrode arrangement above improves the coupling and extraction of the signals through the detection cell volume, resulting in a more precise and sensitive analysis capability. Specifically, the figures show a comparison of the output signals captured by an oscillator between the cell geometry of the preferred embodiment (FIG. 4) and that of a conventional detection cell (FIG. 5). Given an input signal of 300 kHz, 50 $V_{pp}$, the amplitude of the output signal of the preferred embodiment is at 600 kHz, 0.62 $V_{pp}$. A similar input to the conventional electrode arrangement (with the same electrode dimensions and the same detection volume) also produces an output of 600 kHz but at only 0.46 $V_{pp}$.

The voltage amplitude increase in the output signal in the present invention is the result of a better coupling between the electrodes placed in the configuration of the present invention. One reason for this is that both the top and bottom emitting electrodes 100a, 101a are connected to one source of excitation signal, which causes the emitted signal from the top electrode 100a to be repelled and concentrated into the detection area of the channel 102 by the bottom electrode 101a and vice versa. In other words, the electrodes 100a, 101 form a quasi closed conductor (acting as electrostatic images of each other) reflecting the electrical signals into the detection cell volume, thus concentrating and increasing the electric field lines in the detection cell volume. Also, at the receiving electrodes 100b, 101b, the chances of losing signals are reduced as both electrodes 100b and 101b are there to collect the incoming signals. As a result of the increased number of electric field lines in the detection cell volume and the reduced loss of signals to be extracted, improved signal interaction and signal extraction are made possible from every charge passing through the detection cell volume.

It should be noted that the detection cell length determines the signal output. Increasing the detection length by increasing the displacement or separation gap between the electrodes will increase the signal intensity. However, at the same time, it will also reduce resolution or the ability to discern between two separated plugs, which is important in order to identify and quantify analytes of interest. Depending on the particular application, these two parameters (signal intensity vs. resolution) will need to be optimized simultaneously and balanced. In the preferred embodiment, therefore, the displacement between the emitting and receiving electrodes is adjustable by having at least one pair movable along the separation channel. This allows adjustment of the detection limit (efficiency) and/or peak separation (resolution) depending on the demands of the specific application.

A series of experimental analysis were carried out to demonstrate the improvement in the output signal comparing conventional cell geometry and the cell geometry of the present invention. During the experiments, other conditions were kept exactly the same: input signal (sine wave 300 kHz, 50$V_{pp}$), detection length (2 mm), electrode width (1 mm), buffer solutions and samples' concentration. A sample containing four cations at 0.05 mM concentration was analyzed by electrophoresis and the resulting signals were recorded in an electropherogram using a DAQ system. The following were the electrophoretic separation conditions: separation buffer, 10 mM His/tris buffer solution; L injection protocol by applying potential of 4 kV between the first and second sample reservoirs for 2 s, computer controlled switching to run buffer reservoir and the grounded outlet reservoir using 4 kV for separation; sample 0.05 mM cations ($NH_4^+$, $K^+$, $Na^+$, $Li^+$).

Figure 6:
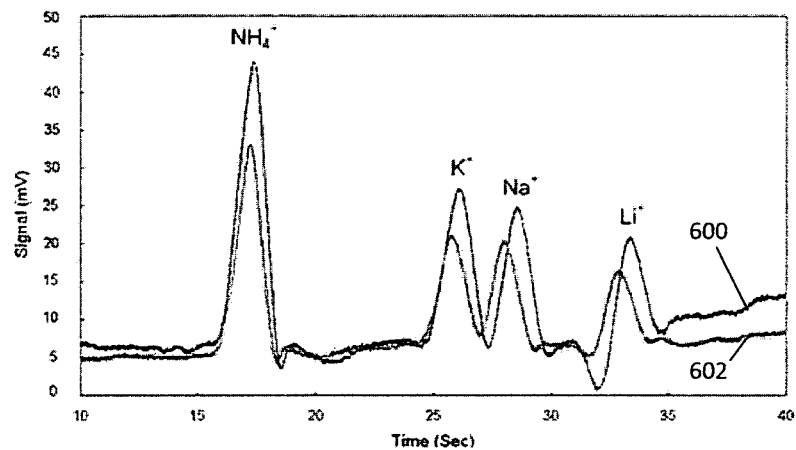
FIG. 6 is a graph comparing the signal intensity obtained using the electrode configuration of the present invention and using a conventional electrode configuration.

FIG. 6 shows the comparison between the electropherogram obtained from the top-bottom configuration of the preferred form (line 600) and the conventional configuration (line 602). The experimental results indicate an average of 20% increase in the peak height or approximately 0.2V increase for every volt of the output signal. For example, for the peak height of $K^+$ at 50 μM concentration, the signal is increased from 20 mV to 28 mV. This means that the ratio concentration/signal has been decreased from 2.5 Km/mV to 1.7 Km/mV. This accordingly improves the detection limit (i.e. a lower concentration of a sample is now sufficient to produce a discernable output).

Figure 7:
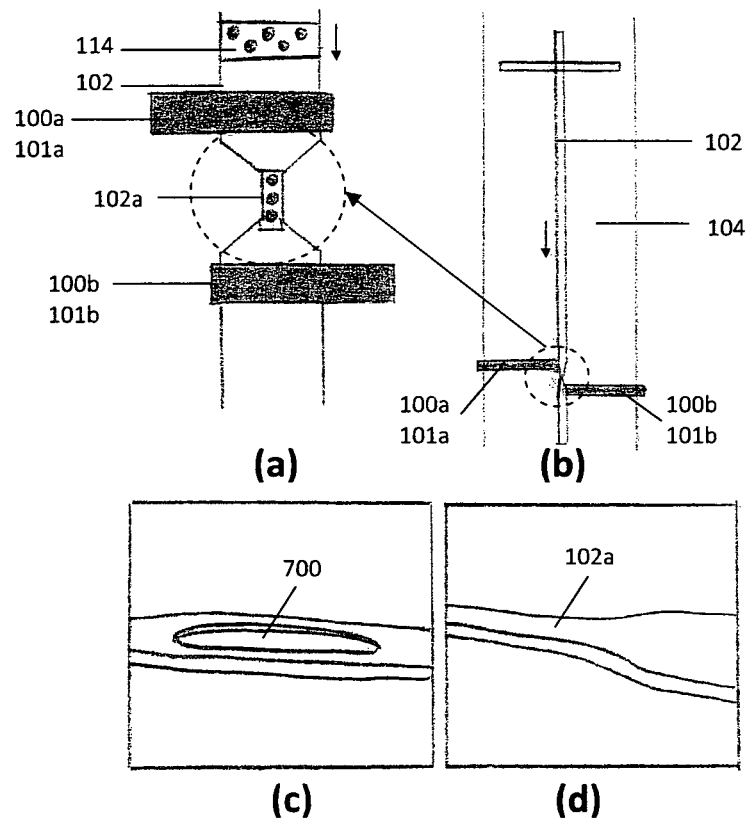
FIGS. 7(a) and (b) are schematics of a restricted-C4D detection cell configuration.
FIGS. 7(c) and (d) are schematics of the geometry of the molds used for hot embossing the restricted detection cell.

In addition to providing a top-bottom configuration, embodiments of the present invention also provide additional improvements to C4D cell geometries. Referring to FIGS. 7(a) and (b), a chip 104 is shown with a separation channel 102, a plug of ions 114 and pairs of detection electrodes 100a, 101a and 100b, 101b. The detection electrodes are shown adjacent the detection cell volume of the separation channel 102, with at least part of the detection cell volume being scaled down to submicron and/or nanosize with a restrictive or narrowed-down channel 102a cross-section/width at or about the detection area. The restrictive channel 102a not only functions to increase resistance but also functions to enlarge the change of resistance from background to analyte. A higher change of resistance over the background signal translates to a higher output signal level i.e. the S/N ratio. The restrictive channel 102a may be fabricated using the molds shown in FIG. 7(c) or (d), which respectively provide two peripheral restrictions (i.e. around an obstruction 700 in the centre of the channel 102) and a central restriction to the channel 102.

Figure 8:
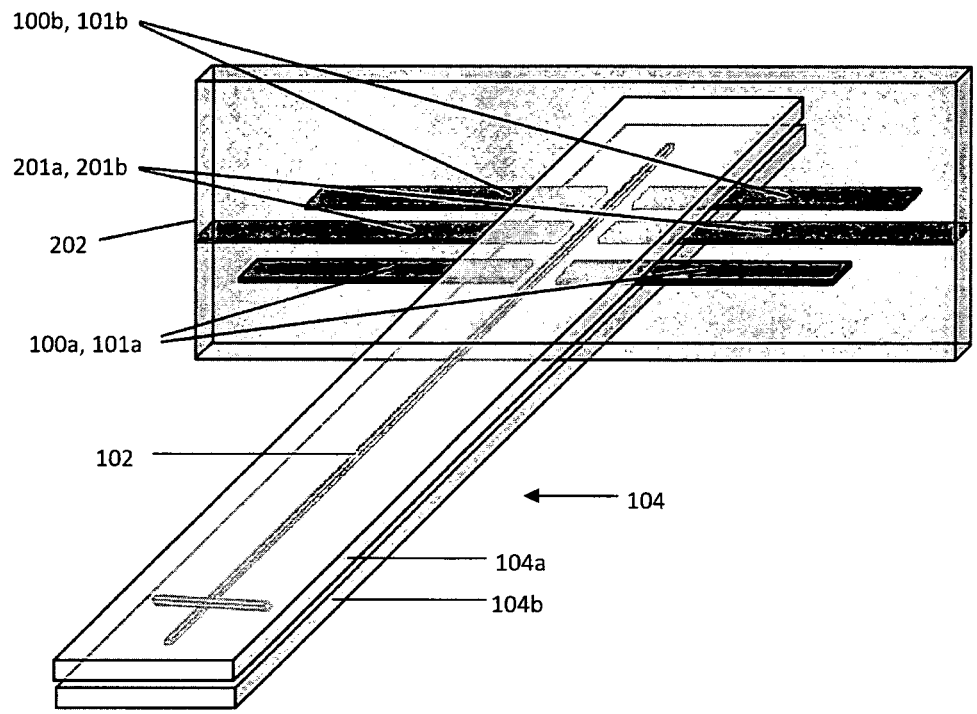
FIG. 8 is a schematic of a further embodiment of the electrode arrangement of the present invention.

In another embodiment, as shown in FIG. 8, the detection cell of the present invention comprises emitting electrodes 100a, 101a, ground shields 201a, 201b and receiving electrodes 100b, 101b that have been integrated into the chip 104 using thermal bonding. The ground shields 201a, 201b in addition to the plane ground shield 202 help to reduce further the stray capacitance due to coupling through the bulk polymer material between the emitting electrodes 100a, 101a, and receiving electrodes 100b, 101b. Each pair of electrodes is positioned laterally in parallel (i.e. the pairs are parallel in the same plane), in close proximity to the channel 102 and are bonded at the same time the channel and top cover of the chip are bonded. In another approach, the electrodes can be bonded between the plastic sheets (top sheet 104a and bottom sheet 104b) that form the chip 104 before the assembly is aligned and bonded to another piece of polymer sheet. A lateral hot embossed groove may be provided to facilitate the alignment before bonding. In this embodiment, the top electrodes are essentially on one side of the channel, and the bottom electrodes are on an opposite side.

Figure 9:
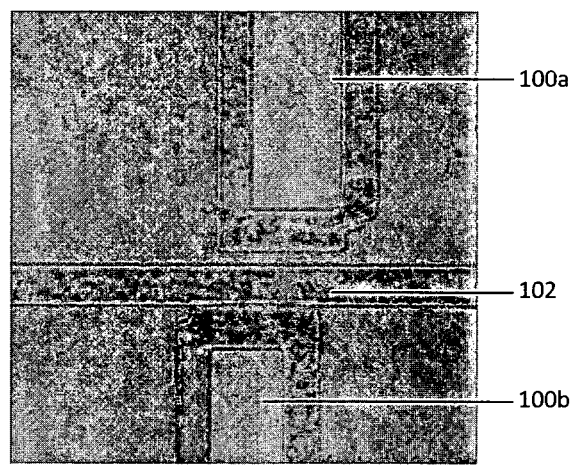
FIG. 9 is an image of electrodes of the present invention formed by hot embossing together with the cross channel prior filling with conductive material.

FIG. 9 shows a modification to the lateral electrode embodiment. In this modification, each lateral pair is in the form of enclosed lateral channels which are in close proximity to the separation channel 102 and which are filled with conductive material (although only one pair is shown in FIG. 9). In particular, the electrodes begin as channels hot embossed into the chip at the same time as when the cross channel is hot embossed, and then sealed. The design and the gap to the channel are tailored using the mold, hot embossing process and bonding conditions. Once the channels are formed and sealed, the channels are connected to reservoirs and are filled via pumps with a conductive material (e.g. silver paint) which, after drying, become conductive electrodes. The closest gap between the electrodes and the channel achieved in this configuration is 5 μm. By optimizing the hot embossing and boding conditions, the gap can be scaled down to even smaller sizes (e.g. 1 μm).

Figure 10:
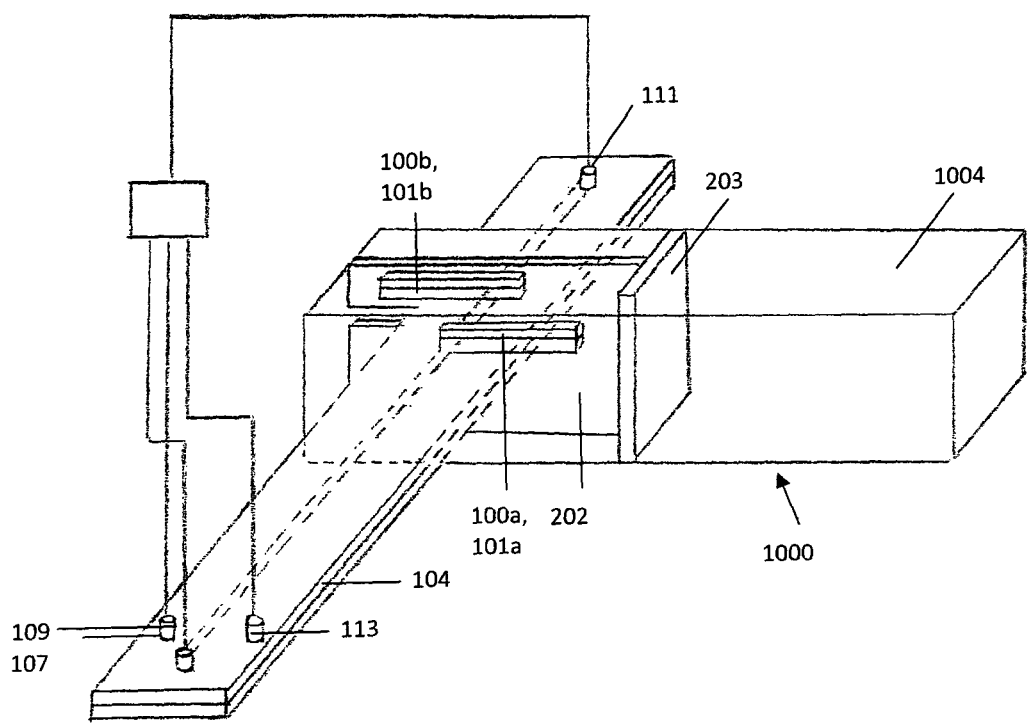
FIG. 10 is a schematic showing a C4D shielded housing.

In addition to a cell electrode geometry, the present invention also comprises a shielded housing for the C4D detector of the electrophoretic system. A schematic of one shielded housing of the detection cell is shown in FIG. 10. The housing 1000 acts as a Faraday shield to shield only the detection cell within the separation channel 102, leaving the rest of the microfluidic chip 104 accessible for input of fluids and application of high voltage for electrophoresis separation. The housing 1000 substantially eliminates interferences from external noise sources, from the DC power applied at the terminus of the channels, and from handling operations, such as sample and reagent injection etc. Specifically, a first ground plane 202 is provided to eliminate direct coupling between the detection electrodes, and a second ground plane 203 is provided to isolate the detection electronics from the C4D electrodes. In the embodiment illustrated, the first and second ground planes 202, 203 are in an anti-parallel (i.e. perpendicular) configuration with respect to each other.

The shielded housing 1000, which is made of metal and which preferably extends perpendicularly to the length of the chip 104, is grounded and includes a cavity 1004 in which the detection electronics and circuit is positioned. The detection electronics are arranged on a circuit that comprises two layers, i.e. top and bottom printed circuit board (PCB) layers. The top layer is isolated from the bottom layer and comprises an operational amplifier and exchangeable feedback resistor to convert current to voltage. A very short coaxial cable transfers the signal from the receiving electrodes through a hole to the top layer. Then, the converted voltage signal is transferred to the bottom layer for rectification, low pass filtering, and offset/gain baseline suppression to bring the level of the output signal to zero.

Figure 11A:
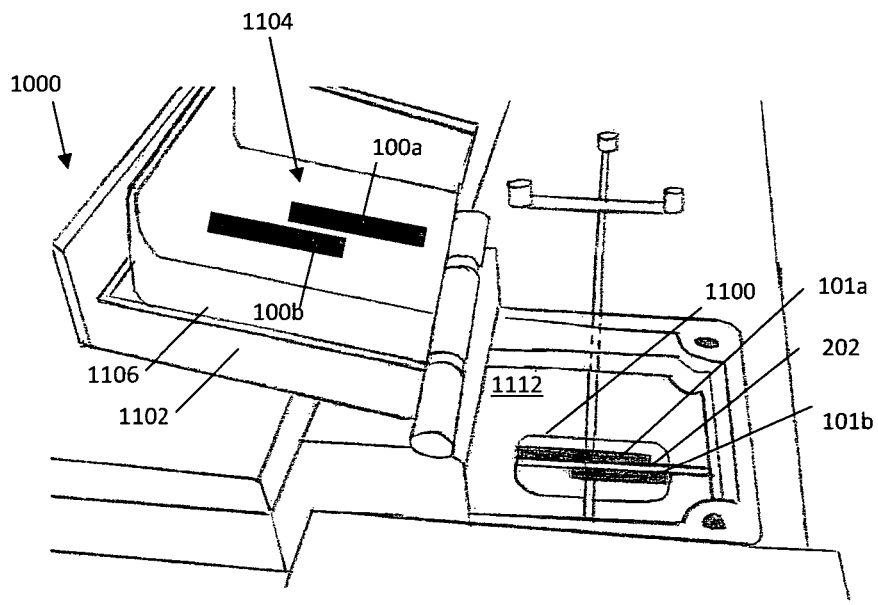
FIG. 11(a) is a schematic of C4D housing showing the top and bottom electrodes disposed on a retractable electrode mechanism.

An alternative shielded housing 1000 is shown in FIG. 11A. As before, the housing 1000 includes top electrodes 100a, 100b and bottom electrodes 101a and 101b together with a ground plane 202. A Faraday shield 1100 is provided to shield the detection electrodes and the detection area between the electrodes. The shielded housing of FIG. 11A further includes a pivotable cover 1102 to allow access to the detection cell. In one embodiment, the cover 1102 includes a retractable electrode mechanism 1104, which is configured to sandwich a microfluidic chip in the housing 1000 and to press the detection electrodes against the chip tightly when the cover is closed so as to achieve closest proximity and to avoid air gaps between the detection electrodes and the separation channel.

Figure 11B:
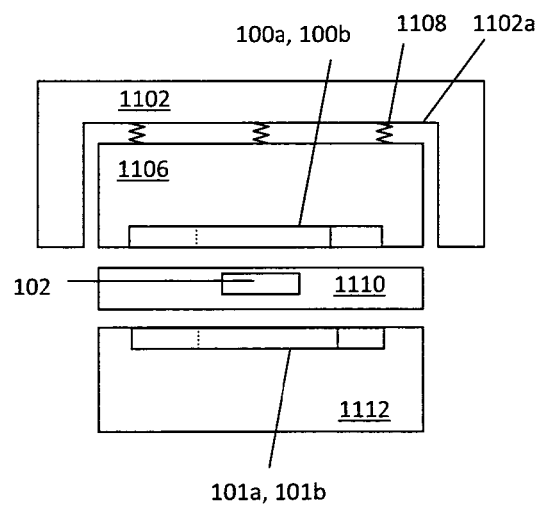
FIG. 11(b) is a cross-section view of the housing of FIG. 11(a) with a microfluidic chip.

The retractable electrode mechanism 1104 of the preferred embodiment includes a holder 1106 that is resiliently coupled to the internal surface 1102a of the cover 1102 and that secures the top emitting and receiving electrodes 100a, 100b. The resilient coupling is by way of springs 1108 as shown in FIG. 11B. FIG. 11B also shows the placement of a microfluidic chip 1110 having a channel 102 in the opening between the cover 1102 and the base 1112 of the opening of the device in or on which the bottom electrodes 101a, 101b are located. The cover 1102, chip 1110 and base 1112 are shown in FIG. 11B having gaps therebetween for clarity. In use, gaps in the arrangement are minimized by having the cover 1102 clamp down so as to press and secure the chip 1110 on the base 1112.

Figure 11C:
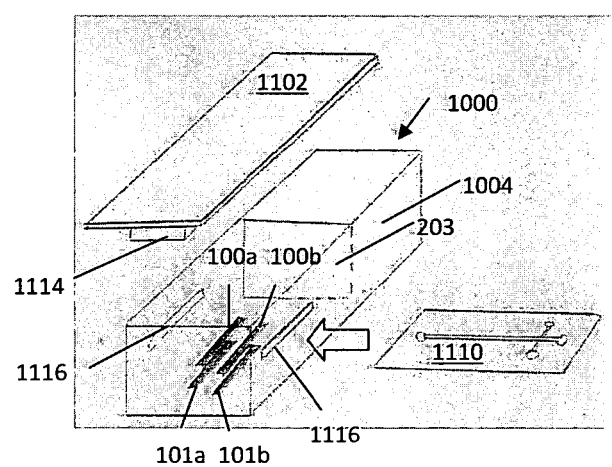
FIG. 11(c) is an alternative embodiment of the shielded housing.

Another alternative embodiment of the shielded housing 1000 is shown in FIG. 11C. The housing 1000 in this embodiment is similar to that of FIG. 10 but includes a detachable cover 1102. The cover 1102 is arranged to press against a resilient spacer 1114, which in turn presses the top electrodes 100a, 100b against the microfluidic chip 1110. This in turn presses against the bottom electrodes 101a, 101b, thus optimizing the proximity of the detection electrodes to the detection area. In this configuration, the chip 1110 is slid into position via slots 1116 in the housing 1000. The top and bottom electrodes 100a, 100b, 101a, 101b are positioned such that when the chip 1110 is slid into position, the top electrodes 100a, 100b are automatically positioned on one side of the chip 1110, while the bottom electrodes 101a, 101b are automatically positioned on the opposite side of the chip 1110.

In the arrangement of the housing 1000 of FIG. 11C, the chip 1110 is placed as close as possible to the electronics in the housing 1000. The housing therefore includes a cavity or compartment 1004 to contain the electronic components of the device, like the embodiment of FIG. 10. A first ground shield (not shown) is arranged between the emitting and receiving electrodes while a second ground shield 203 is arranged to separate the detection cell from the electronic components. This arrangement allows minimal signal losses and interference from noise signals from outside the detection cell.

Figure 12A:
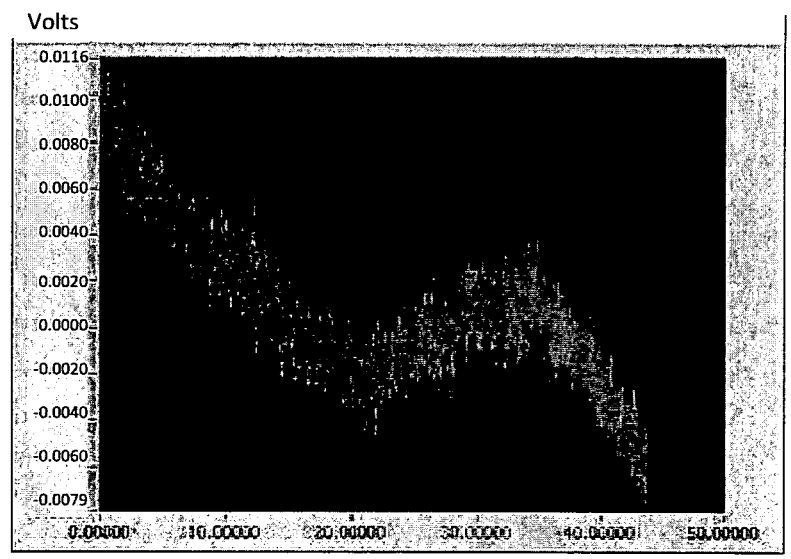
FIGS. 12(a) and (b) are graphs respectively showing noise level before using the shielded housing and after using the shielded housing.
Figure 12B:
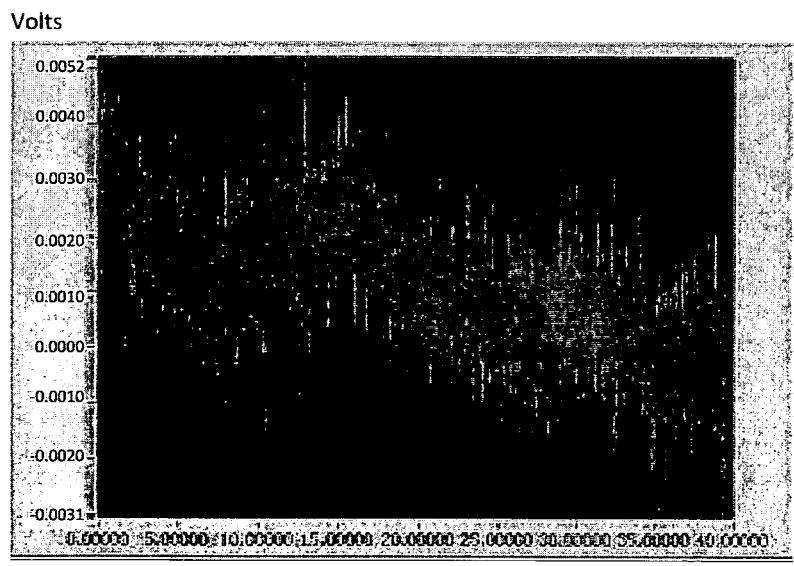

FIGS. 12(a) and (b) respectively show a comparison of the noise level without and with the shielded housing. Without using the shielded housing, the level of noise for a signal of 300 kHz, $20V_{pp}$ is between 3 to 4 mV, while with the shielded housing, this value is reduced to 1 to 2 mV.

Figure 13:
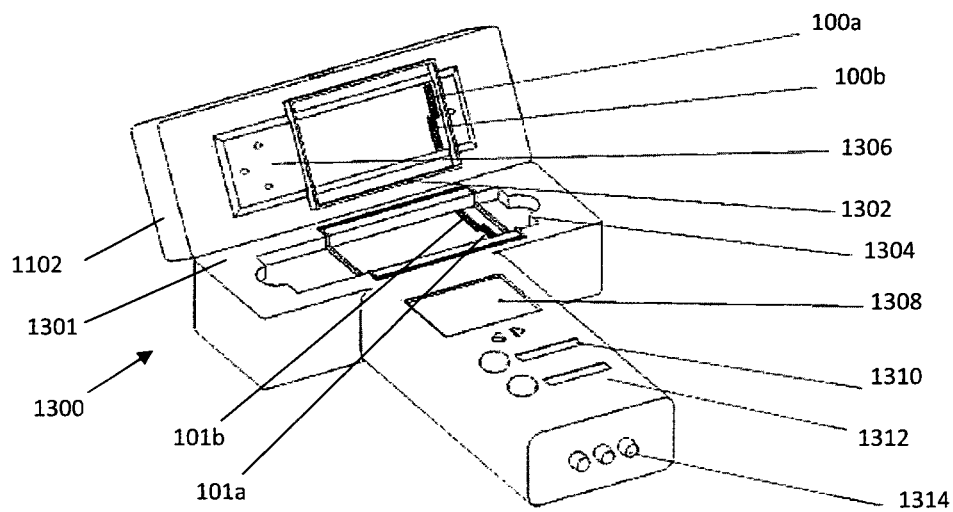
FIG. 13 is a schematic diagram of the LOC-C4D portable electrophoretic system.

In the exemplary embodiment of FIG. 13, the invention provides a portable electrophoretic system 1300 that is configured to sandwich a chip (not shown) that is locatable in an opening 1304 (herein chip slot 1304) on a platform 1301. The chip slot 1304 is configured to allow the chip to be moved along the slot 1304 to allow a repositioning of the detection area of the chip.

The portable system 1300 includes a metal housing 1302 for shielding the detection cell of the chip. The metal housing 1302 is provided in two halves: one half extending from the cover 1102 and enclosing the top electrodes 100a, 100b, and the other half located in the base of the chip slot 1304. Once the cover 1102 is closed, the two halves make up a complete housing. Much like the embodiment of FIG. 11A, a retractable electrode mechanism is provided in the cover 1102 to retract the top electrodes 100a, 100b so that they make perfect contact with the chip when the cover clamps and secures the chip on a base of the slot 1304. The portable system 1300 also includes bottom electrodes 101a, 101b on or adjacent the base of the chip slot 1304. The arrangement of the detection electrodes on the cover and the base are such that when a chip is placed in the chip slot 1304 and the cover 1102 is in its closed position, the detection electrodes are in an operative arrangement described earlier with reference to FIG. 3.

Next to the housing 1302 are encased detector electronics which are shielded from the detection cell and from external noise to provide minimal noise and/or signal loss and easy transport. The portable device 1300 also includes a switching mechanism for alternating electrodes in operation or toggling the voltage in the reservoirs between sample injection and ion separation using high-voltage DC electrodes 1306 for electrophoresis. Also provided in the portable system 1300 are: a display 1308, an optional ground electrode acting as an electric ground to shield the detection electrodes from direct coupling, and an electronic signal processing unit comprising a signal generator and amplifier (including a potentiometer 1310 for baseline suppression and a resonator 1312 for AC generation), and a miniaturized high voltage power supply system. Specifically, for the receiving side, a battery-powered current-to-voltage converter is provided adjacent and connected to the receiving electrodes, and a rectifier, low-pass filter, and offset circuit are connected to the current-to-voltage converter. For the emitting side, a battery-powered alternating current function generator is provided adjacent and connected to the emitting electrodes, together with a miniaturized high voltage power supply. Connections 1314 are provided to interface the portable device 1300 with a computing device. By providing portability, detection or analysis can be carried out at the point of use, which obviates the need to transport samples back to a laboratory.

In one embodiment, the portable device 1300 further comprises wireless capabilities. Specifically, the device 1300 may be configured to send signals wirelessly to a personal digital assistant (PDA), a smart phone, a portable meter or the like. This may be implemented using electronics having a Bluetooth or WiFi module configured to send and/or receive signals wirelessly. The device 1300 may also operate wirelessly such that sample injections and switching on and off of the device may be controlled wirelessly.

Figure 14:
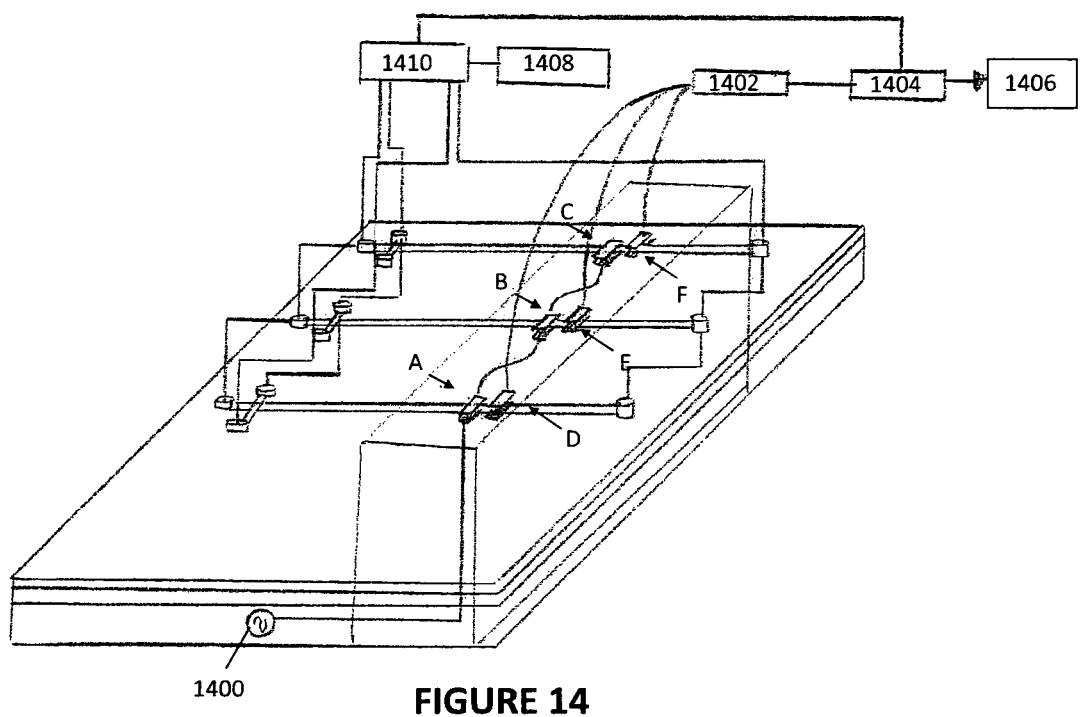
FIG. 14 is a schematic of a multiple detection cell arrangement for parallel multiple analysis.

In other embodiments, such as that shown in FIG. 14, the portable device is provided with multiple detection capabilities using multiple pairs of top-bottom electrodes where all the emitting pairs A, B and C are connected together to a single input signal 1400 and all the receiving pairs D, E and F are connected to individual receiving amplifiers and processing electronics 1402, and using a single analog-to-digital converter (ADC) 1404 with multiple inputs and a DQA system 1406 with multiple electropherograms, each corresponding to one sensor and analysis. This may be carried out by providing a microchip having multiple enclosed parallel cross channels all in one chip, which is inserted into the chip slot of the portable device to be operatively coupled in parallel to the multiple emitting and receiving electrodes in the device. A miniaturized high voltage power supply system 1408 and relays 1410 are used in this embodiment to selectively activate the separation electrophoresis in the multiple enclosed parallel cross channels.

Figure 15:
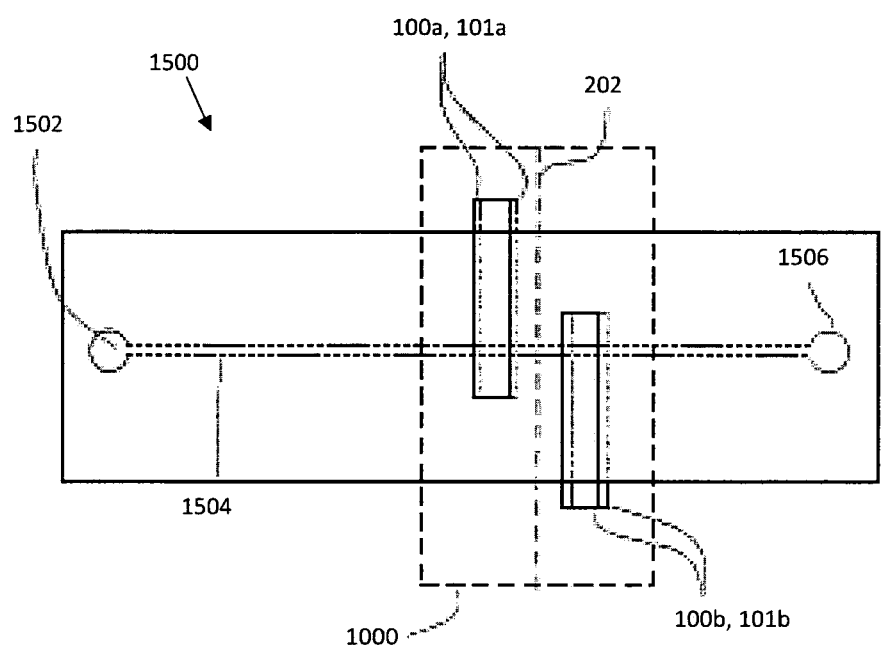
FIG. 15 is a schematic diagram showing an on-line contactless conductivity system.

Another alternative embodiment of the C4D detection cell according to the present invention is an application of the top-bottom configuration in an on-line conductivity monitoring device, e.g. for monitoring total dissolved ionized solids in water samples. This device is shown schematically as 1500 in FIG. 15. The device 1500 includes the top and bottom emitting electrodes 100a, 101a, and the top and bottom receiving electrodes 100b, 101b. A ground plane 202 is also provided together with a shielded housing 1000. Fluid for monitoring will enter the device at an inlet 1502, flow down the microfluidic channel 1504 to the outlet 1506. As will be appreciated by skilled persons, the on-line monitoring device has applications in, for example, on-line water quality control, on-line monitoring of dialysis water treatment system, on-line conductivity monitoring of haemodialysis process, chemical concentration control, etc.

EXPERIMENTS

The experiments for the present invention began with the fabrication of microfluidic chips. Specifically, thin microfluidic chips were fabricated by hot embossing on polycarbonate (PC) or polymethyl methacrylate (PMMA) sheets with a thickness of only 125 μm. To emboss PC and PMMA, a hard stamp carrying the microfluidic channel features was used. The stamp and polymer were heated together on a hot plate to a temperature slightly above the $T_g$. After the stamp polymer sandwich reached the embossing temperature, a uniform pressure of 3.2-4.8 kN was applied to the chip area for 10 minutes. With the force still applied, the system was cooled below the $T_g$. On reaching this temperature, the force was released and the embossed substrate was de-molded. Sealing of the embossed channels was performed by bonding a second substrate where inlet reservoirs have been drilled in. Bonding was preformed by applying a uniform pressure, exerting 1.6 kN to the chip area at 140° C. for 20 minutes.

Electrophoresis is performed on the plastic chips. Initially the channels were preconditioned and then filled through one of the reservoirs with separation buffer: 10 to 30 mM MES-His (2-N-morpholinoethanesulfonic acid/histidine), 2 mM 18-Crown-6, and pH 6.4. Reservoirs 107, 109 and 111 (see FIG. 10) were filled with the electrophoretic run buffer solution, while reservoir 113 was filled with the sample mixture (target ions dissolved in the separation buffer).

After an initial loading, the sample was injected into the separation channel by applying potentials of +1000 V (cations) or −1000 V (anions) for 1 s to 5 s between reservoirs 109 and 113. This voltage drove the ions electrokinetically through the channels intersection, which were subsequently separated by applying a separation voltage of 2,000 to 10,000V between the reservoirs 107 and 111.

The C4D detector was formed using a pair of emitting and receiving electrodes of 1-2 mm in width displaced by 0.3-2 mm in distance. Typical AC actuation signals for the thin plastic chips and top-bottom electrode design are 10-100$V_{pp}$ at 100 to 300 kHz.

Figure 16:
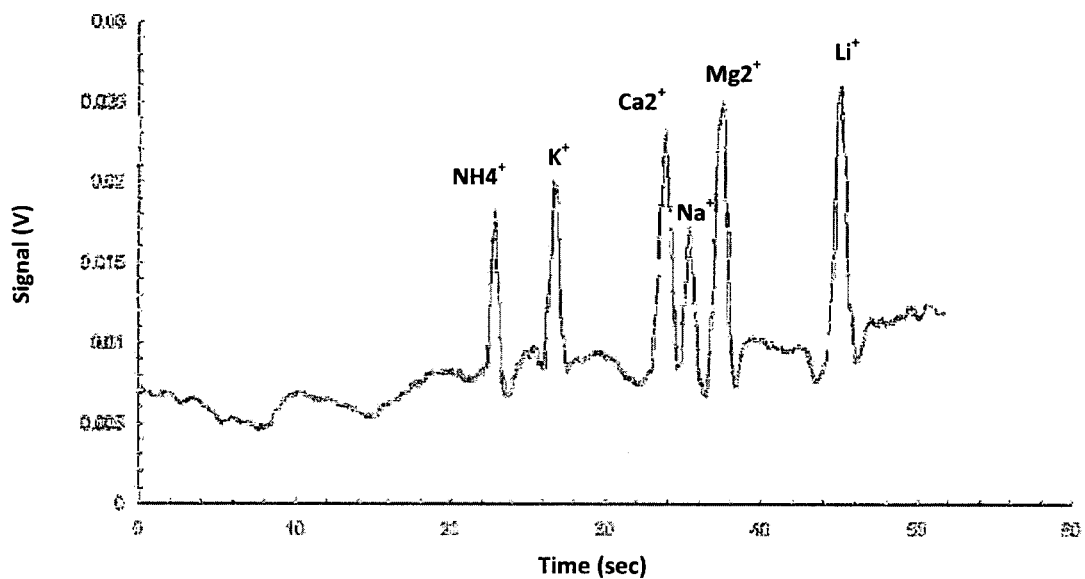
FIG. 16 is a graph showing electrophoretic analysis and conductometric detection of inorganic cations in a standard mixture containing 0.1 mM of each ion with electrode distance at 0.3 mm.

Experiments were then carried out to detect sample inorganic cations and anions. For the experiment to detect cations, the concentration of each ion was 0.1 mM (6 mg/L). as shown in FIG. 16. The experiment conditions were: injection voltage, 3000V; injection time 2 s; separation voltage 4000V; running buffer 30 mM MES-His pH 6; sinus input waveform with a frequency of 300 kHz and 50$V_{pp}$; electrode distance 0.5 mm; and electrode width 1 mm. For the experiment to detect anions, the concentration of each ion was 1 mM. The experiment conditions were: microfluidic chip 130/128 mm total/effective length; electrolyte solution 30 mM MES/His, 2 mM 18-crown-6, pH 6; injection voltage, 1 kV for 1 s; separation voltage, 7 kV; C4D detector: sine waveform of 300 kHz and 15 $V_{pp}$; electrode distance, 1 mm; electrode width, 1 mm.

Figure 17:
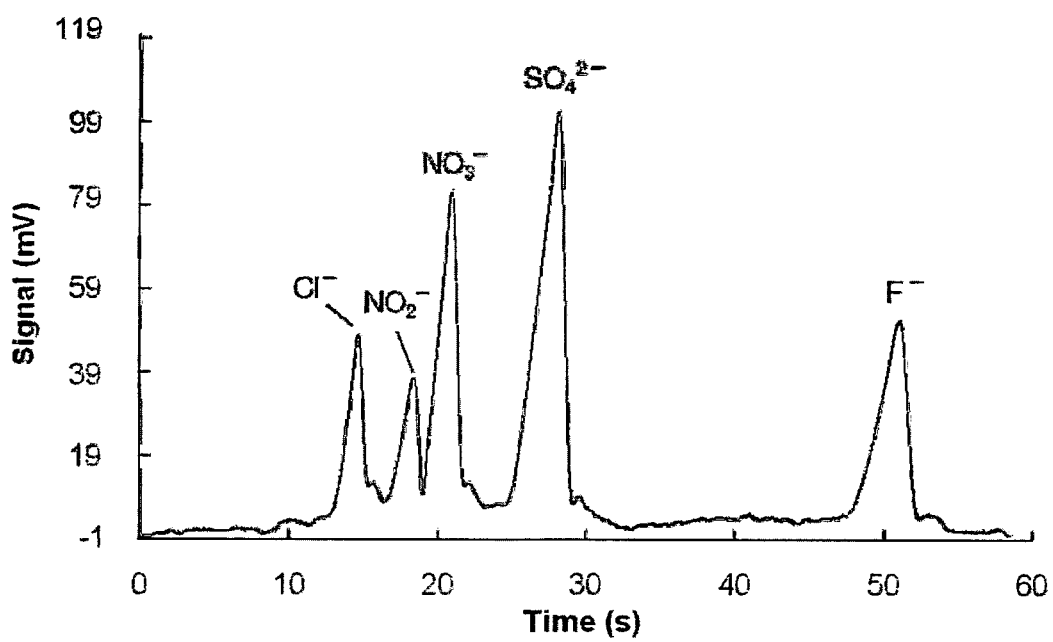
FIG. 17 is a graph showing electrophoretic analysis and conductometric detection of inorganic anions in a standard mixture containing 1 mM of each ion with electrode distance at 1 mm.

The resulting electropherogram of cations at concentration of 0.1 mM (6 mg/L) is shown in FIG. 16 (x-axis in seconds and y-axis in volts). All analyte peaks of interest were baseline resolved. The electropherogram of anions at concentration of 1 mM is shown in FIG. 17 (x-axis in seconds and y-axis in milivolts). Both figures show accurate determinations of the target ions.

Figure 18:
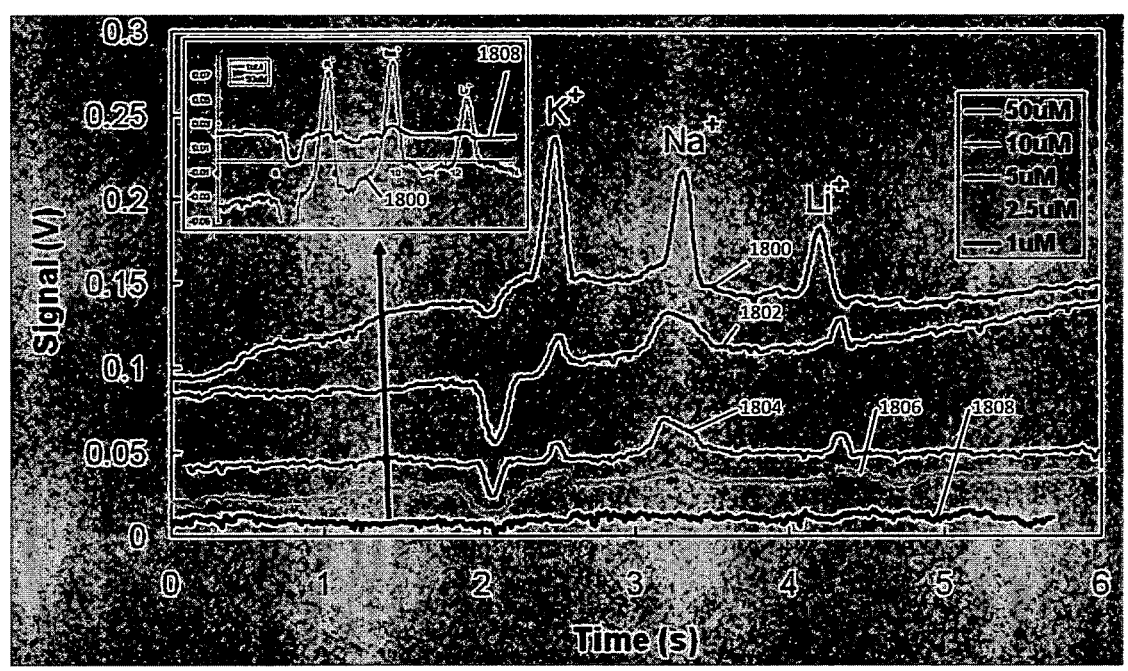
FIG. 18 is a graph showing electrophoretic analysis and conductometric detection of inorganic cations in a standard mixture containing 1-50 µM of each ion.

Referring to FIG. 18, the electrophoretic analysis and conductometric detection were carried out for inorganic cations in a standard mixture containing 1-50 µM of each ion. The experiment operating conditions were: injection voltage 4000 V; injection time 1-3 s; separation voltage 10 kV; running buffer 10 mM MES-His pH 6; sinus input waveform with a frequency of 300 kHz and $20V_{pp}$; electrode distance 0.5 mm; electrode width 1 mm. The graph depicted shows the detected spectra for the following concentrations: 50 µM—line 1800, 10 µM—line 1802, 5 µM—line 1804, 2.5 µM—line 1806 and 1 µM—line 1808 (x-axis in seconds and y-axis in volts). FIG. 18 also shows the detection of cations at the limit of detection (LOD) of the experimental set up, i.e. LOD of 0.001 mM, 1 µM. The inset of FIG. 18 shows a magnified spectrum of the 1 µM sample (line 1808) compared to that of the 50 µM sample (line 1800).

Advantages arising from the present invention will be apparent from the foregoing description. For example, it will be appreciated that the top-bottom cell geometry allows electric field lines from each emitting electrode to be confined or focused in the detection cell volume, and signals from the detection cell volume to be optimally extracted by the receiving electrodes. This provides the present invention with improved sensitivity (i.e. the ability to detect smaller amounts of samples) over existing microfluidic based electrophoretic C4D systems. It is important to be able to provide good sensitivity at the same time as portability and be able to extend the analytical method to a bigger range of analytes including those minor elements like heavy metals.

Sensitivity is also improved by embodiments of the invention that use thin microfluidic chips, as they allow the detection electrodes to be in very close proximity to the channel to improve capacitive coupling between the AC voltage and the solution in the detection cell. This can be contrasted with known systems that use thick microfluidic chips (i.e. >1 mm thickness). When the microchips are made of thick polymer sheets, the electrodes are placed at larger distance from the channel, which causes the capacitance to drop. To address this, conventional systems provide a higher frequency input AC signal to achieve sufficient coupling between the electrodes. In general, this leads to higher stray capacitance and overall loss in sensitivity. Another conventional alternative is to increase the magnitude of the AC signal from typical values of 20-50V to $300V_{pp}$. Such a voltage, however, is difficult to handle from the point of view of safety and is impractical in portable systems.

The portable C4D-LOC analytical system with optimized sensitivity requires lower inputs of voltage than previously employed to achieve low detection limits. That is to say, by increasing the electrodes' capacitance by placing the detection electrodes in a top-bottom configuration and in close proximity to the detection cell volume, and optionally improving the signal-to-noise ratio by using a ground plane in a shielded housing to eliminate crosstalk and external electrical noise, the present invention is feasibly operable on a lower power. This is a particularly important advantage for portable systems since a high AC voltage is dangerous to handle and the instrumentation required to produce such high signals can be prohibitively bulky.

Where a shielded housing is implemented, further improvements in sensitivity and thus LOD can be obtained since the C4D detection cell is further isolated from the high voltage, environmental noise and artifacts. This can be contrasted with known C4D detectors that do not implement a shielded housing and that accordingly suffer from much higher LODs.

Where the electrode arrangement of the invention is implemented using external electrodes (i.e. not integrated with the chip) with adjustable distance integrated into a shielded housing, a robust and low-cost process is provided for the fabrication of the detection cell. This avoids the cost and complexity of micro-fabrication processes.

The foregoing describes preferred embodiments, which, as will be understood by those skilled in the art, may be subject to variations or modifications in design, construction or operation without departing from the scope of the claims. For example, while most embodiments have been described with reference to electrophoresis, this is not essential. As described with reference to FIG. 15, the detection cell or detection system may be used for non-electrophoresis purposes (e.g. liquid chromatography, stand alone conductivity sensor). Also, in terms of electrode arrangement, while the figures show electrodes aligned to the channel, this is not essential. All that is required is for the electrodes to cover and be adjacent the channel so that signal coupling is achieved as described earlier. The position of the electrodes with respect the channel is not critical and signal coupling can be accomplished when the electrodes cover totally or partially the channel width. It will also be appreciated that while the term top-bottom has been used to describe the electrode geometry, the invention is not limited to the top and bottom areas of the channel; an opposing-sides placement as shown in FIG. 8 is also encompassed. Also, the electrodes need not be positioned flat on the microfluidic chip but may, where necessary or desired, be positioned vertically (i.e. so the edges of the electrodes are adjacent the channel). The above variations, for instance, are intended to be covered by the scope of the claims.

The invention claimed is:

1. A contactless conductivity detection cell comprising:
   a microfluidic chip having a channel defined by channel walls,
   first and second emitting electrodes, and
   first and second receiving electrodes,
   a first ground plane between the emitting electrodes and the receiving electrodes,
   a grounded metal housing containing the emitting electrodes, the receiving electrodes and the first ground plane, and
   a second ground plane configured to shield the emitting electrodes and the receiving electrodes from interferences from electronic components housed in the grounded metal housing,
   wherein the first emitting electrode and the first receiving electrode are adjacent a first channel wall, and the second emitting electrode and the second receiving electrode are adjacent a second channel wall, the second channel wall being opposite the first channel wall;
   wherein the first emitting electrode and the first receiving electrode are arranged adjacent one side of the channel and spaced from the channel; and
   wherein the second emitting electrode and the second receiving electrode are arranged adjacent an opposite side of the channel.

2. The detection cell of claim 1, wherein the emitting electrodes and receiving electrodes are substantially planar and substantially parallel to each other.

3. The detection cell of claim 1, wherein the emitting electrodes are placed one on top and one at the bottom of the channel, and are configured to act as electrostatic images of each other to concentrate and focus signals from each other into a detection cell volume of the detection cell.

4. The detection cell of claim 1, wherein the receiving electrodes are placed one on top and one at the bottom of the channel, and are configured to act as electrostatic images of each other to extract coupled signals from a detection cell volume of the detection cell.

5. The detection cell of claim 1, wherein the electrodes are each positioned at a distance of between 75 μm and 1000 μm from the channel.

6. The detection cell of claim 1, wherein the microfluidic chip has a thickness in the range of 30 μm to 1 mm.

7. The detection cell of claim 1, wherein at least part of the channel between the emitting electrodes and the receiving electrodes has a restricted submicron-sized or nano-sized width, wherein the first emitting electrode and the first receiving electrode are arranged on or in a top plate of the microfluidic chip, and wherein the second emitting electrode and the second receiving electrode are adjacent a base of the channel.

8. The detection cell of claim 1, further comprising multiple parallel channels, each channel having a pair of emitting electrodes and a pair of receiving electrodes, wherein all of the emitting electrode pairs are connected to a single input.

9. A portable electrophoretic contactless conductivity detection system comprising:
   a platform having an opening configured to receive a microfluidic chip having a channel defined by channel walls,
   a cover configured to close at least part of the opening,
   first and second emitting electrodes, and
   first and second receiving electrodes, the first emitting electrode and the first receiving electrode being positioned on or adjacent an internal surface of the cover, the cover including a holder on an internal surface, and wherein the first emitting electrode and the first receiving electrode are positioned on the holder, and the holder is resiliently coupled to the cover and configured to press the first emitting electrode and the first receiving electrode against a microfluidic chip,
   wherein the first emitting electrode and the first receiving electrode are configured to be positioned adjacent a first channel wall, and the second emitting electrode and the second receiving electrode are configured to be positioned adjacent a second channel wall, the second channel wall being opposite the first channel wall;
   wherein the first emitting electrode and the first receiving electrode are arranged adjacent one side of the channel and spaced from the channel; and
   wherein the second emitting electrode and the second receiving electrode are arranged adjacent an opposite side of the channel.

10. The detection system of claim 9, wherein the cover is configured to secure at least part of a microfluidic chip between the cover and a base of the opening, wherein the second emitting electrode and the second receiving electrode are positioned on or adjacent the base of the opening, and wherein the cover is selected from a group consisting of: a pivotable cover and a detachable cover.

11. The detection system of claim 9, further comprising one or more slots to allow a microfluidic chip to be inserted into the opening.

12. The detection system of claim 9, wherein the emitting electrodes and/or the receiving electrodes are movable along the channel, and wherein the opening is configured to allow a microfluidic chip to be movable within the opening.

13. The detection system of claim 9 further comprising detection electronics arranged on a circuit that comprises a top layer and a bottom layer, the top layer being isolated from the bottom layer.

14. A portable electrophoretic contactless conductivity detection system comprising:
   a platform having an opening configured to receive a microfluidic chip having a channel defined by channel walls,
   a cover configured to close at least part of the opening,
   first and second emitting electrodes, and
   first and second receiving electrodes,
   a current-to-voltage converter adjacent and connected to the receiving electrodes, and a rectifier, low-pass filter, and offset circuit connected to the current-to-voltage converter, and further comprising an alternating current function generator adjacent and connected to the emitting electrodes, and a miniaturized high voltage power supply,
   wherein the first emitting electrode and the first receiving electrode are configured to be positioned adjacent a first channel wall, and the second emitting electrode and the second receiving electrode are configured to be positioned adjacent a second channel wall, the second channel wall being opposite the first channel wall;
   wherein the first emitting electrode and the first receiving electrode are arranged adjacent one side of the channel and spaced from the channel; and
   wherein the second emitting electrode and the second receiving electrode are arranged adjacent an opposite side of the channel.

15. A capacitive coupled contactless conductivity detection cell comprising:
   a housing including a microfluidic chip having a channel,
   detection electrodes placed in a top-bottom geometry in the housing, the detection electrodes comprising two emitting electrodes and two receiving electrodes, the emitting electrodes being placed one on top and one at the bottom of the channel and being configured to act as electrostatic images of each other to concentrate and focus signals from each other into a detection cell volume in a detection area, the receiving electrodes also being placed one on top and one at the bottom of the channel, spaced from the channel but close to the channel, and being configured to act as electrostatic images of each other to extract the signals collectively from the detection cell volume of the detection cell located within the housing,
   a Faraday shield, and
   a grounded metal housing,
   wherein the electrodes are shielded from direct crosstalk or external noise by the Faraday shield and the grounded metal housing, and
   wherein the two emitting electrodes and two receiving electrodes are separated by the Faraday shield and located in the grounded metal housing, wherein the emitting and receiving electrodes are movable by a cover to adjust the detection cell volume, and wherein the detection area is adjustable by moving the microfluidic chip within the emitting and receiving electrodes.

16. A portable capacitive coupled contactless conductivity detection device in which the detection cell according to claim 15 is incorporated.

* * * * *